(12) United States Patent
Ikeda et al.

(10) Patent No.: US 7,940,382 B2
(45) Date of Patent: May 10, 2011

(54) METHOD FOR INSPECTING DEFECT OF HOLLOW FIBER POROUS MEMBRANE, DEFECT INSPECTION EQUIPMENT AND PRODUCTION METHOD

(75) Inventors: Makoto Ikeda, Tokyo (JP); Ryuhei Uchiyama, Tokyo (JP); Osamu Nagasawa, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 76 days.

(21) Appl. No.: 12/528,177

(22) PCT Filed: Mar. 16, 2007

(86) PCT No.: PCT/JP2007/055369
§ 371 (c)(1),
(2), (4) Date: Aug. 21, 2009

(87) PCT Pub. No.: WO2008/126186
PCT Pub. Date: Oct. 23, 2008

(65) Prior Publication Data
US 2010/0117250 A1    May 13, 2010

(51) Int. Cl.
G01N 21/00 (2006.01)
(52) U.S. Cl. ................... 356/237.1; 356/239.1
(58) Field of Classification Search ........... 356/237.1, 356/239.1, 241.1, 241.4
See application file for complete search history.

(56) References Cited

U.S. PATENT DOCUMENTS

| | | | | |
|---|---|---|---|---|
| 4,021,217 A | * | 5/1977 | Bondybey et al. | 65/378 |
| 4,357,826 A | * | 11/1982 | Tahara et al. | 73/37.7 |
| 4,924,087 A | * | 5/1990 | Bailey et al. | 356/73.1 |
| 5,598,262 A | * | 1/1997 | Jutard et al. | 356/239.1 |
| 6,064,478 A | * | 5/2000 | Paul et al. | 356/237.1 |

FOREIGN PATENT DOCUMENTS

| | | |
|---|---|---|
| JP | 62-096838 | 5/1987 |
| JP | 05-312727 | 11/1993 |
| JP | 06-099043 | 4/1994 |
| JP | 09-152323 | 6/1997 |
| JP | 10-282016 | 10/1998 |
| JP | 2006-212622 | 8/2006 |
| JP | 2007-114187 | 5/2007 |

OTHER PUBLICATIONS

English language Abstract of JP 09-152323, Jun. 10, 1997.
English language Abstract of JP 06-099043, Apr. 12, 1994.
English language Abstract of JP 2006-212622, Aug. 17, 2006.
English language Abstract of JP 62-096838, May 6, 1987.
English language Abstract of JP 05-312727, Nov. 22, 1993.
English language Abstract of JP 10-282016, Oct. 23, 1998.
English language Abstract of JP 2007-114187, May 10, 2007.

* cited by examiner

Primary Examiner — Roy Punnoose
(74) Attorney, Agent, or Firm — Greenblum & Bernstein P.L.C.

(57) ABSTRACT

A method for inspecting a defect of a hollow fiber porous membrane having substantially uniform, continuous inner hollow portions comprises steps for introducing a part of the hollow fiber porous membrane into an irradiation chamber, for irradiating the hollow fiber porous membrane with light from the outside in the irradiation chamber, and for detecting light exiting the hollow fiber porous membrane on the outside of the irradiation chamber.

10 Claims, 3 Drawing Sheets

(a)

(b)

(c)

(a)

(b)

(a)

(b)

METHOD FOR INSPECTING DEFECT OF HOLLOW FIBER POROUS MEMBRANE, DEFECT INSPECTION EQUIPMENT AND PRODUCTION METHOD

TECHNICAL FIELD

The present invention relates to a method for inspecting a defect of a hollow fiber porous membrane, defect inspection equipment, and a production method.

BACKGROUND ART

Conventionally, in the internal-defect inspection of a hollow fiber porous membrane, a visual inspection cannot be performed because the shape of the hollow fiber porous membrane is cylindrical and opaque, and therefore, a destructive inspection method has been used, wherein an internal pressure is applied to destruct the hollow fiber porous membrane. The destructive inspection can be performed by pressurizing a hollow portion from both ends of a continuous single fiber. Since the hollow portion is usually pressurized after a hollow fiber membrane module is formed, the inspection is performed in the units of module products and therefore the loss due to a defect increases, causing a decrease in the yield.

On the other hand, Patent Document 1 has proposed an on-line inspection method of a hollow fiber membrane using transmitted light. However, the technique of Patent Document 1 is a technique for eliminating the effect of direct light by using a polarizing filter, and detecting an un-whitening defect with regard to the light passing through a hollow fiber porous membrane on the opposite side of an irradiation plate. This technique can shield the neither scattered light nor transmitted light at an edge portion of a cylindrical hollow fiber porous membrane and therefore cannot be adapted for the inspection of an internal defect causing a pinhole of a target hollow fiber porous membrane.

Patent Document JP-A-9-152323

DISCLOSURE OF THE INVENTION

Problems to be Solved by the Invention

As described above, due to a need for quality improvement or yield improvement of the hollow fiber porous membrane, it is desirable to provide an inspection method capable of performing on-line inspection of an internal defect of the hollow fiber porous membrane in the production steps. However, there is a problem with the case of the hollow fiber porous membrane, in that only a destructive inspection is possible in the method for inspecting an internal defect because the hollow fiber porous membrane is opaque and cylindrical.

Means for Solving the Problems

After conducting intensive study and observation to solve the above-described problems, the present inventor has found that in the hollow fiber porous membrane, light emitted from the outside of the hollow fiber porous membrane will propagate a relatively long distance through a continuous hollow portion, and that the light propagating through the hollow portion seeps to the outside as a pseudo light source, and furthermore that its light intensity provides a substantially constant brightness throughout the circumferential direction. Thus, the present inventor has come to an invention of a practical defect inspection method and inspection equipment, wherein light propagating through a hollow portion and seeping to the outside is imaged outside an irradiation chamber. Furthermore, the present inventor has also invented a method of producing a hollow fiber porous membrane characterized by obtaining a bundle of hollow fiber membranes, a defective fiber of which has been removed using the method for inspecting a defect of a hollow fiber porous membrane according to the present invention.

Namely, the configuration of the present invention is as follows.

(1) A method for inspecting a defect of a hollow fiber porous membrane having a substantially uniform, continuous inner hollow portion, the method comprising the steps of: introducing a part of the hollow fiber porous membrane into an irradiation chamber; irradiating the hollow fiber porous membrane in the irradiation chamber with light from the outside of the irradiation chamber; and detecting light exiting the hollow fiber porous membrane on the outside of the irradiation chamber.

(2) The method according to the above (1) further comprising the step of imaging an optical image of light exiting the hollow fiber porous membrane on the outside of the irradiation chamber, and image-processing the imaged signal.

(3) The method according to the above (1) or (2), wherein a distance from an exterior of the irradiation chamber to an imaging position is 0.5 to 5.0 times an inner diameter of the hollow fiber porous membrane.

(4) Equipment for inspecting a defect of a hollow fiber porous membrane having a substantially uniform, continuous inner hollow portion, the equipment comprising: an irradiation chamber including a light shielding means for preventing irradiation light from directly leaking to the outside of the irradiation chamber and an irradiation means for irradiating the hollow fiber porous membrane with light from the outside of the irradiation means; an imaging means for imaging an optical image of light exiting the hollow fiber porous membrane on the outside of the irradiation chamber by introducing light, which is emitted in the irradiation chamber, into a hollow portion of the hollow fiber porous membrane; and an image processing means for detecting a defect of the hollow fiber porous membrane by processing a signal of the imaging means.

(5) The equipment according to the above (4), wherein the light irradiating means comprises a light source having an emission opening for optical fibers arranged on a straight line.

(6) A method for producing hollow fiber porous membranes, the method comprising the step of obtaining a bundle of hollow fiber membranes, a defective fiber of which has been removed using the method for inspecting a defect of a hollow fiber porous membrane according to any one of the above (1) to (3).

The present invention solves the above-described problems. Namely, the present invention relates to a method and equipment capable of performing on-line inspection on an internal defect of a hollow fiber membrane accurately and also on a plurality of hollow fiber membranes simultaneously. According to another aspect of the present invention, the present invention relates to a method for producing hollow fiber porous membranes capable of selectively removing a detected defective portion.

The irradiation chamber includes; the irradiation means for emitting light from the outside of a hollow fiber porous membrane; and the light shielding means for preventing irradiation light from directly leaking to the outside of the irradiation chamber. The irradiation means may be of any type as long as it can irradiate the hollow fiber porous membrane with light, however, an irradiation means using white light is preferable because it can increase the absolute quantity of light intensity.

Transmitting light from the light source by means of an optical fiber is preferable because this prevents heat generation due to irradiation light with respect to the hollow fiber membrane. An irradiation means with a light source having an emission opening for optical fibers arranged on a straight line is preferable because this can irradiate a plurality of hollow fiber membranes simultaneously.

The inner surface of the irradiation chamber is preferably mirror-finished so as to be able to repeatedly reflect irradiation light and efficiently irradiate the hollow fiber porous membrane with these irradiation light and reflected light.

The light shielding means of the irradiation chamber prevents light from leaking along the periphery of the hollow fiber membrane, and preferably maintains a gap larger than the outer diameter of the hollow fiber porous membrane by 10 to 50% and shields light without damaging the hollow fiber porous membrane.

The distance from an exterior of the irradiation chamber to the imaging means is preferably 0.5 to 5.0 times the inner diameter of the hollow fiber. Within this range, it is possible to measure an internal defect of the target hollow fiber membrane accurately.

BEST MODE FOR CARRYING OUT THE INVENTION

First, with regard to the present invention, a configuration is described with reference to the accompanying drawings.

FIG. 1(a) is a schematic diagram showing a configuration of an embodiment of equipment for inspecting a defect of a hollow fiber porous membrane according to the present invention. FIG. 1(b) is a partial explanatory view (camera position) of FIG. 1(a), and FIG. 1(c) is a cross sectional view of the hollow fiber porous membrane.

In FIG. 1(a), a hollow fiber porous membrane 1 serving as an object is introduced into an irradiation chamber 4, and light is emitted from the outside of the irradiation chamber using a line-type fiber illuminating device 2, preferably from an emission opening 3 for optical fibers arranged on a straight line. In order to effectively use the emitted light, the inner wall of the irradiation chamber 4 preferably comprises a light reflecting plate. In order to prevent light, other than the light propagating through a hollow portion of the hollow fiber membrane 1, from leaking to the outside of the irradiation chamber, the wall of the irradiation chamber in the traveling direction of the hollow fiber porous membrane may have a through-hole 4a with a gap larger than the outer diameter of the hollow fiber porous membrane by 10 to 50% opened in a plate of 1 to 2 mm thickness so as to be able to shield light without damaging the hollow fiber porous membrane. Outside the irradiation chamber, there may be provided cameras 6a, 6b (see FIG. 1(b)) for imaging an optical image emitted to the outside of the hollow fiber porous membrane 1, image processing devices 12a, 12b for detecting a defect of the hollow fiber membrane 1 serving as the object by processing the output signals of the cameras 6a, 6b, and the like.

A distance d between an entrance of the irradiation chamber 4 in the longitudinal direction of the hollow fiber membrane 1, i.e., an exterior of the irradiation chamber, and the cameras 6a, 6b serving as the imaging means is preferably set 0.5 to 5.0 times the inner diameter of the hollow fiber porous membrane. The line-type illuminating device 2 may comprise a light source having the emission opening 3 linearly arranged. Signals of the image processing devices 12a, 12b are sent to a defect removal system 13, where a detected defective portion is selectively removed and as a result, a bundle of hollow fiber porous membranes whose defect has been removed can be obtained.

Next, the configuration requirements of the present invention are specifically described.

An object to be inspected is the hollow fiber porous membrane 1. Preferably, the hollow fiber porous membrane 1 is a tube-like object with the membrane outer diameter of 0.5 to 5.0 mm and the membrane thickness of 0.1 to 1.0 mm and includes therein a hollow portion 1a of 0.4 to 4.5 mm diameter, as shown in FIG. 1(c). The quality of the material is not limited in particular, but organic polymers such as, polyolefine such as polyethylene, polycarbonate, polysulfone, polyethersulfone, polyacrylonitrile, polyvinylidene fluoride, and polyether ketone-based materials may be used. The continuous hollow portion of the hollow fiber porous membrane 1 can be applicable to a gas, such as an inert gas or air, or transparent liquids, such as water or an organic aqueous solution.

The light emitted from the outside to the hollow fiber porous membrane 1 having therein a substantially uniform hollow portion propagates through the continuous hollow portion. The light propagating through the hollow portion is emitted to the outside as a pseudo light source, resulting in circumferentially unidirectional light with a substantially constant quantity of light. Defects to be inspected include internal defects such as a through-pinhole or non-through pinhole of the hollow fiber porous membrane, or a foreign matter, or a prominent fluctuation in the outer diameter of the membrane, and the like, but not limited thereto, and any defect to be optically captured can be a target to be inspected.

For the line-type illuminating device 2, a lamp, such as a halogen lamp or a metal halide lamp, having a high brightness and relatively long life is employed as the light source, and is installed proximate to the hollow fiber porous membrane 1 so as to efficiently apply light from the emission opening 3 to the hollow fiber porous membrane 1 serving as the object. Moreover, the line-type illuminating device 2 preferably includes an emission opening for optical fibers linearly arranged. The linearly arrangement of the emission opening makes it possible to simultaneously irradiate a plurality of hollow fiber porous membranes with light.

The irradiation chamber 4 is made of a metal with a thickness of 1 to 2 mm, and the inner wall thereof may be miller-finished so that light emitted from the line-type optical fiber illuminating device 2 may be efficiently captured by the hollow fiber porous membrane 1. The irradiation chamber 4 includes a through-hole 4a serving as a passage of the hollow fiber porous membrane 1 in the traveling direction of the hollow fiber porous membrane 1, and the diameter of the through-hole 4a is preferably set wider than the outer diameter of the hollow fiber porous membrane 1 by approximately 10 to 50%. The light within the irradiation chamber is thereby shielded without damaging the hollow fiber porous membrane.

Moreover, as a method for further improving the shielding effect, a method is more preferable wherein a gap between the hollow fiber porous membrane 1 and the through-hole is substantially reduced by running the hollow fiber porous membrane 1 at an angle with respect to the through-hole. When the hollow fiber porous membrane 1 is in contact with a part of the through-hole at an angle, joining a rubber-like material or a fibrous material to the through-hole is also effective in terms of light shielding properties and damage prevention.

The cameras 6a, 6b are preferably comprised using a line-sensor camera. This allows for inspection even when the hollow fiber porous membrane 1 serving as an object moves at high speed. For the imaging position, a position, where the distance d from the entrance of the irradiation chamber to the imaging position in the longitudinal direction of the hollow fiber porous membrane 1 serving as an object is 0.5 to 5.0 times the inner diameter of the hollow fiber porous membrane, is preferable. Within this range, it is possible to accurately measure an internal defect of the target hollow fiber membrane. If the distance d is equal to or greater than 0.5 times the inner diameter of the hollow fiber porous membrane, high-precision measurement can be made because the measurement is unlikely to be affected by the direct light or the like leaking out of the irradiation chamber. If the distance d is within 5 times the inner diameter of the hollow fiber porous membrane, the light intensity required for measurement can be secured.

The signals picked up by the cameras 6a, 6b are processed by the image processing devices 12a, 12b so as to able to selectively detect only an internal defect. Furthermore, the signals detected by the image processing devices 12a, 12b are transferred to the hollow fiber porous membrane removing system 13, where a defect portion can be selectively removed. The defect removal system can obtain a string bundle of hollow fiber porous membranes, a defect portion of which has been removed using a method for marking a defect detected portion or a method for switching winders, for example.

EXAMPLES

Hereinafter, the present invention will be described based on examples (see FIGS. 1 to 4). The present invention is not limited in any way by the following examples.

Example 1

A spinning dope containing polysulfone (Udel P-3500 manufactured by SOLVAY) as the raw material and N-methylpyrrolidone as a solvent was injected, together with water of an internal liquid, in the form of a hollow fiber in the air and was then solidified in a coagulation bath, thereby producing a hollow fiber porous membrane using 16 spinning spindles at a line velocity of 20 m/min. Prior to being wound up after taken out of the coagulation bath and through a washing process, the hollow fiber porous membrane 1 (with outer diameter of 1.4 mm and inner diameter of 0.8 mm) was introduced into the irradiation chamber 4 (to serve as the through-hole 4a with a hole size of 1.8 mm opened at 1 mm intervals when the upper lid is closed) manufactured by SUS, the irradiation chamber including therein the line-type optical fiber illuminating device 2 (metal halide illuminating device: MLDS250 (250 W) manufactured by Iwasaki Electric Co., Ltd.) and a line-type light guide: GF8-1L1500 R-S100 manufactured by Sumita Optical Glass, Inc., as shown in FIG. 2(a). After closing the upper lid, the line-type optical fiber illuminating device 2 was caused to irradiate from the emission opening 3 at an output power of 60%, from the outside of the hollow fiber porous membrane. An image propagating through the hollow portion of the hollow fiber porous membrane and exiting to the outside thereof was captured with the line-sensor camera 6a (lens: Micro Nikkor 55 mm F 2.8 manufactured by NIKON CORP.) under the conditions: imaging distance of 275 mm, imaging resolution of 50 µm/pixel (the same for X and Y axes). At this time, the imaging surface of the hollow fiber porous membrane 1 was caused to contact the through-hole 4a, and the distance d was set to 2 mm. The normal output value of the line-sensor camera was set to 25 and a threshold value was set to 40, and binarization processing was performed by the image processing device, and thereby an image of a defective hollow fiber membrane shown in FIG. 2(b) (left side) was automatically detected. Moreover, from a brightness profile of FIG. 2(b) (right side) obtained by digitizing the output values of the line-sensor camera into 0 to 511 levels, a non-through pinhole that is an internal defect could be distinguished with a sufficient accuracy of S/N ratio of 3.0. In FIG. 2(b) (right side), reference numeral 8 indicates the brightness profile of an internal defect and reference numeral 9 indicates the brightness profile of a normal portion.

Moreover, a detection image detected by the defect inspection equipment is sent to image inspection equipment 14 in the defective removal system 13 of FIG. 4, and then the winding roll for a string bundle of hollow fiber porous membranes containing an internal defect exceeding the threshold value is temporarily switched from a winding roll 16 to an auxiliary roll 17 by automatically sliding a switching guide 15, thereby succeeding in obtaining a fiber bundle whose defective portion has been selectively removed.

Examples 2 to 6

The defect targeted at in the method of the present invention is a non-through defect (a cavity enclosed in the hollow fiber porous membrane) that will be destroyed by a practical operating pressure. However, it is difficult to experimentally form a non-through defect and therefore a model experiment was conducted by artificially opening a pinhole in the hollow fiber porous membrane which was spun in Example 1. The same defect detection device as that of Example 1 was used. The detection condition of each example is shown in Table 1.

A hollow fiber membrane having a pinhole opened therein was introduced into the defect detection device and was then imaged with the imaging distance d of the line-sensor camera 6a in a range of 0.2 to 5.6 mm, and then the output values of the line-sensor camera were digitized into 0 to 511 levels, which were then image-processed to obtain a brightness profile. A ratio of the output values of an un-through pinhole and an artificially opened through-pinhole is calculated from the output values of the line-sensor camera of Examples 1 and 3, and the output value of an un-through pinhole was estimated by multiplying this ration to the output values of the artificially opened through-pinholes of Examples 2 to 6, and then the SN ratio of an un-through pinhole was calculated as a trial from a ratio of the resultant estimated value and the normal output value of the hollow fiber porous membrane. Table 1 shows the results.

In Table 1, for the light intensity of a defect portion, Example 1 indicates the light intensity of a non-through defect, and Examples 2 to 6 and Comparative Example 1 (to be described later) indicate the light intensity of a through defect portion that is artificially opened with a needle. The normal light intensity is the light intensity of a normal portion of a hollow fiber porous membrane. The estimate value of an un-through portion is a calculated value obtained by estimating the light intensity of a non-through defect portion from the light intensity of a through defect portion in Examples 2 to 6 and Comparative Example 1 (to be described later), and was calculated by the following formulas.

A ratio A of a non-through defect and a through defect: light intensity of an un-through portion ((light intensity of a defect portion−normal light intensity) of Example 1)/light intensity of a through-portion ((light intensity of a defect portion−normal light intensity) of Example 3)=(75−25)/(370−25)=0.145.

The estimate value of an un-through portion: ((light intensity of a defect portion−normal light intensity) of Examples 2 to 6 *A+light intensity of a normal portion).

The SN ratio is calculated as (light intensity of a non-through defect)/(normal light intensity). In Example 1, the SN ratio is (light intensity of a defect portion)/(normal light intensity), while in Examples 2 to 6 and Comparative Example 1 (to be described later), the SN ratio is indicated as (estimate value of an un-through portion)/(normal light intensity).

For the S/N ratio, considering variations in the normal light intensity and noise, the threshold value for detecting a defect is desirably set equal to or greater than 1.5 times the normal light intensity. Therefore, the S/N ratio equal to or greater then 1.5 would make it possible to detect a defect accurately. Even if the SN ratio falls below 1.5, the S/N ratio equal to or greater than 1.2 would enable the measurement by improving the accuracy in shielding the outside light. In Examples 1 to 4, the SN ratio is equal to or greater then 1.5 and a defect portion could be detected without being affected by variations in the normal light intensity. The brightness profile at a defective position of Example 3 is shown in FIG. 3(a). In FIG. 3(a), reference numeral 8 indicates the brightness profile of an internal defect and reference numeral 9 indicates the brightness profile of a normal portion.

In Example 5, the SN ratio decreased below 1.5 due to an effect of light leaking out of the irradiation chamber and the like, thus degrading the measurement accuracy. In Example 6, the non-through defect could be detected accurately, but the light intensity of a normal hollow fiber porous membrane was less than 15. Therefore, it is difficult for the line-sensor camera to recognize a hollow fiber porous membrane, and the measurement of fluctuations or the like in the fiber diameter cannot be made.

Comparative Example 1

A model experiment was conducted using the same defective fiber as those of Examples 2 to 6. A polarizing filter was put on the same line-type optical fiber illuminating device 2 as the one used in Example 1, and the hollow fiber porous membrane 1 was passed over the polarizing filter, and then the upper lid was removed. Under this condition, the hollow fiber porous membrane 1 was imaged with the line-sensor camera via another orthogonal polarizing filter. The output values of the line-sensor camera were digitized into 0 to 511 levels and a brightness profile was obtained. The SN ratio of Comparative Example 1 calculated by estimating the output value of an un-through pinhole as with Examples 2 to 6 is shown in Table 1. Moreover, the brightness profile of a defective position of Comparative Example 1 is shown in FIG. 3(b). In FIG. 3(b), reference numeral 8 indicates the brightness profile of an internal defect, reference numeral 9 indicates the brightness profile of a normal portion, and reference numeral 10 indicates the brightness profile of an edge portion. In Comparative Example 1, although the direct light can be eliminated using the polarizing filter, an edge portion of the hollow fiber porous membrane shines, making the measurement difficult and decreasing the SN ratio less than 1.2.

TABLE 1

| detection | inner diameter d (mm) | of hollow fiber porous membrane (mm) | d/inner diameter | luminance profile | output value of line-sensor camera ||| SN ratio | observation result |
| | | | | | light intensity of defective portion | normal light intensity | estimate value of no-through portion | | |
| --- | --- | --- | --- | --- | --- | --- | --- | --- | --- |
| Example 1 | 2.0 | 0.8 | 2.5 | FIG. 2(b) | 75 | 25 | — | 3.0 | good |
| Example 2 | 0.5 | 0.8 | 0.5 | — | 420 | 70 | 121 | 1.7 | good |
| Example 3 | 2.0 | 0.8 | 2.5 | FIG. 3(a) | 370 | 25 | 75 | 3.0 | good |
| Example 4 | 4.0 | 0.8 | 5.0 | — | 255 | 15 | 50 | 3.3 | good |
| Example 5 | 0.2 | 0.8 | 0.3 | — | 480 | 150 | 198 | 1.3 | acceptable |
| Example 6 | 5.6 | 0.8 | 7.0 | — | 140 | 7 | 26 | 3.7 | good |
| Comparative Example 1 | — | 0.8 | — | FIG. 3(b) | 180 | 110 | 120 | 1.1 | difficult |

Industrial Applicability

A method for detecting a defect of a hollow fiber porous membrane, defect detection equipment, and a production method according to the present invention can be suitably utilized in a wide range of industrial fields where a defect-free hollow fiber porous membrane needs to be produced.

DESCRIPTION OF REFERENCE NUMERALS

Figure 1:
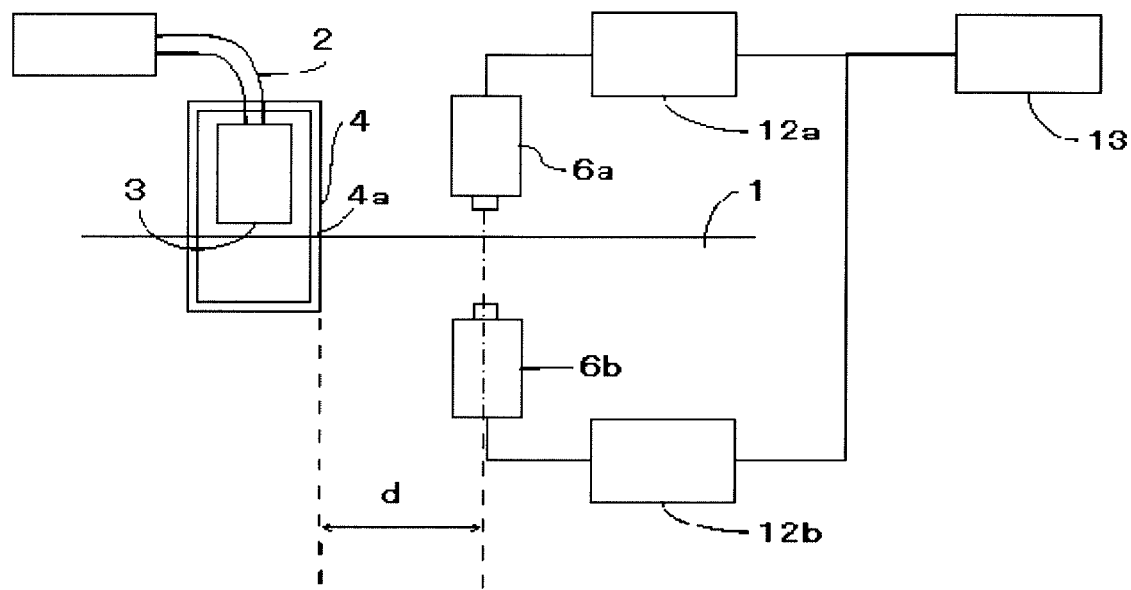
FIG. 1(a) is a schematic diagram of equipment for detecting a defect of a hollow fiber porous membrane according to the present invention.
FIG. 1(b) is a part (camera position) of the schematic diagram of FIG. 1(a).
FIG. 1(c) is a cross sectional view of a hollow fiber porous membrane.
Figure 1:
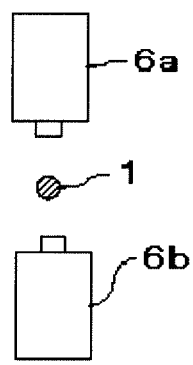
Figure 1:
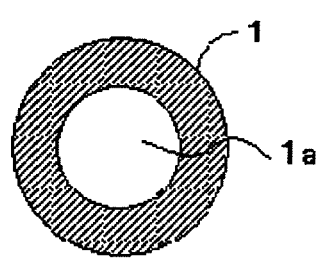
Figure 2:
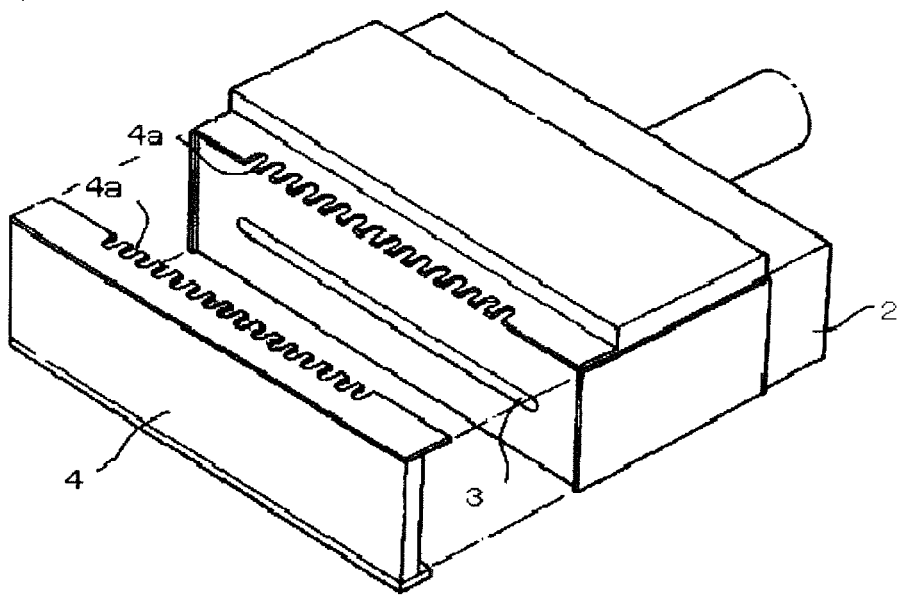
FIG. 2(a) is a schematic diagram of an irradiation chamber of Example 1.
FIG. 2(b) shows an image of a non-through defect automatically detected in Example 1 and a brightness profile of a defective position.
Figure 2:
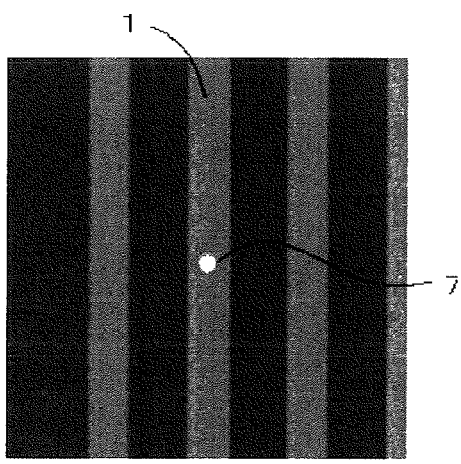
Figure 2:
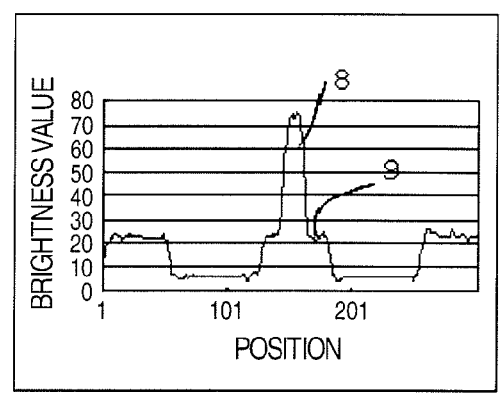
Figure 3:
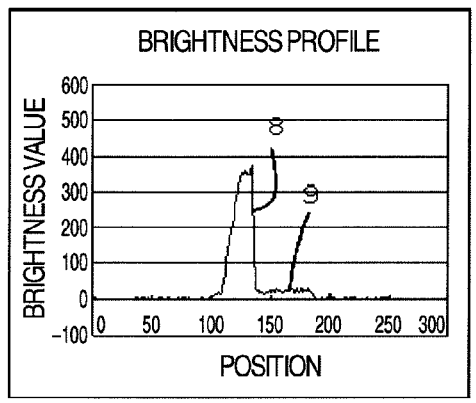
FIG. 3(a) is a brightness profile at a defective position of Example 3.
FIG. 3(b) is a brightness profile at a defective position of Comparative Example 1.
Figure 3:
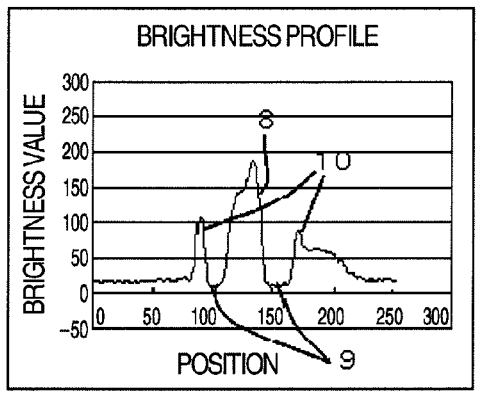
Figure 4:
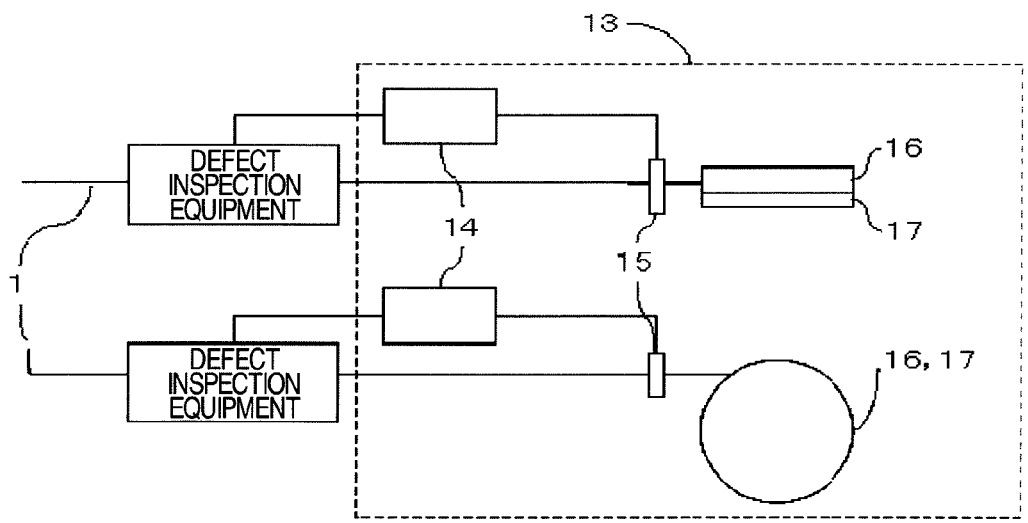
FIG. 4 is a schematic diagram (example) of a defect removal system.

1: hollow fiber porous membrane, 1a: hollow portion of hollow fiber porous membrane, 2: line-type optical fiber illuminating device, 3: emission opening, 4: irradiation chamber, 4a: through-hole, 6a, 6b: camera (color camera), 7: image of internal defect, 8: brightness profile of internal defect, 9: brightness profile of normal portion, 10: brightness profile of edge portion, 12a, 12b: image processing device, 13: defect removal system, 14: image inspection equipment, 15: switching guide, 16: winding roll, 17: auxiliary roll

The invention claimed is:

1. A method for inspecting a defect of a hollow fiber porous membrane having a substantially uniform, continuous inner hollow portion, the method comprising the steps of:
    introducing a part of the hollow fiber porous membrane into an irradiation chamber;
    irradiating the hollow fiber porous membrane in the irradiation chamber with light from an outside of the irradiation chamber; and
    detecting light exiting the hollow fiber porous membrane on an outside of the irradiation chamber.

2. The method according to claim 1, further comprising the step of imaging an optical image of the light exiting the hollow fiber porous membrane on the outside of the irradiation chamber, and image-processing the imaged signal.

3. The method according to claim 2, wherein a distance from an exterior of the irradiation chamber to an imaging position is 0.5 to 5.0 times an inner diameter of the hollow fiber porous membrane.

4. A method for producing a hollow fiber porous membrane, the method comprising the step of obtaining a bundle of hollow fiber membranes, a defective fiber of which has been removed using the method for inspecting a defect of the hollow fiber porous membrane according to claim 3.

5. A method for producing a hollow fiber porous membrane, the method comprising the step of obtaining a bundle of hollow fiber membranes, a defective fiber of which has been removed using the method for inspecting a defect of the hollow fiber porous membrane according to claim 2.

6. The method according to claim 1, wherein a distance from an exterior of the irradiation chamber to an imaging position is 0.5 to 5.0 times an inner diameter of the hollow fiber porous membrane.

7. A method for producing a hollow fiber porous membrane, the method comprising the step of obtaining a bundle of hollow fiber membranes, a defective fiber of which has been removed using the method for inspecting a defect of the hollow fiber porous membrane according to claim 6.

8. A method for producing a hollow fiber porous membrane, the method comprising the step of obtaining a bundle of hollow fiber membranes, a defective fiber of which has been removed using the method for inspecting a defect of the hollow fiber porous membrane according to claim 1.

9. Equipment for inspecting a defect of a hollow fiber porous membrane having a substantially uniform, continuous inner hollow portion, the equipment comprising:
    an irradiation chamber including a light shielding means for preventing irradiation light from directly leaking to the outside of the irradiation chamber and an irradiation means for irradiating the hollow fiber porous membrane with light from an outside of the irradiation means;
    an imaging means for imaging an optical image of light exiting the hollow fiber porous membrane on the outside of the irradiation chamber by introducing light, which is emitted in the irradiation chamber, into a hollow portion of the hollow fiber porous membrane; and
    an image processing means for detecting a defect of the hollow fiber porous membrane by processing a signal of the imaging means.

10. The equipment according to claim 9, wherein the light irradiating means comprises a light source having an emission opening for optical fibers arranged on a straight line.

* * * * *